(12) United States Patent
Gelber

(10) Patent No.: US 7,498,129 B2
(45) Date of Patent: Mar. 3, 2009

(54) MYELOMA CELL AND OVARIAN CANCER CELL SURFACE GLYCOPROTEINS, ANTIBODIES THERETO, AND USES THEREOF

(75) Inventor: Cohava Gelber, Hartsdale, NY (US)

(73) Assignee: ImmunoCellular Therapeutics, Ltd., Woodland Hills, CA (US)

( * ) Notice: Subject to any disclaimer, the term of this patent is extended or adjusted under 35 U.S.C. 154(b) by 263 days.

(21) Appl. No.: 11/332,849

(22) Filed: Jan. 13, 2006

(65) Prior Publication Data

US 2006/0165678 A1 Jul. 27, 2006

Related U.S. Application Data

(60) Continuation of application No. 09/995,522, filed on Nov. 28, 2001, now Pat. No. 6,986,891, which is a division of application No. 09/374,367, filed on Aug. 13, 1999, now Pat. No. 6,376,654.

(51) Int. Cl.
*C12Q 1/00* (2006.01)
*G01N 33/53* (2006.01)

(52) U.S. Cl. .............................. 435/4; 435/7.1; 435/7.23

(58) Field of Classification Search ................... None
See application file for complete search history.

(56) References Cited

FOREIGN PATENT DOCUMENTS

| WO | 88/03954 | 6/1988 |
|---|---|---|
| WO | 94/05329 | 3/1994 |
| WO | 96/26964 | 9/1996 |
| WO | 96/40295 | 12/1996 |

OTHER PUBLICATIONS

Auranen et al., Int J Gynecol Cancer. vol. 17, p. 1000-8, abstract, 2007.*
Sturgeon C. Clinical Chemistry, vol. 48 p. 1151-1159, 2002.*
D. Avichezer et al., 1977, "Immunoreactivities of Polyclonal and Monoclonal Anti-T and Anti-Tn Antibodies with Human Carcinoma Cells, Grown In Vitro and in a Zenograft Model", *Int. J. Cancer*, 72:119-127.
S. Miotti et al., 1999 "Level of Anti-Mouse-Antibody Response Induced by Bi-Specific Monoclonal Antibody OC/TR in Ovarian-Carcinoma Patients is Associated with Longer Survival", *Int. J. Cancer*, 84-62-68.
J. A. Francisco et al., 1997, "In Vivo Efficacy and Toxicity of a Single-Chain Immunotoxin Targeted to CD40", *Blood*, 89:4493-4500.

C.F.M. Molthoff et al., 1997, "Escalating Protein Doses of Chimeric Monoclonal Antibody Mov18 Immunoglobulin G. In Ovarian Carcinoma Patients: A Phase I Study", *Cancer Supplement*, 80:2712-2720.
E. Kievit et al., 1997, "Determination of Tumor-Related Factors of Influence on the Uptake of the Monoclonal Antibody 323/A3 in Experimental Human Ovarian Cancer", *Int. J. Cancer*, 71:237-245.
K.O. Lloyd et al., 1997, "Isolation and Characterization of Ovarian Cancer Antigen CA 125 using a New Monoclonal Antibody (VK-8): Identification as a Mucin-Type Molecule", *Int. J. Cancer*, 71:842-580.
A. van Dalen, 1999, "BR-MA, OM-MA, GI-MA and CEA: Clinical Evaluation Using the IMMULITE Analyzer", *Tumore Biology*, 20:117-129.
G. Gebauer et al., 1999, "IMMULITE® OM-MA Assay: A Useful Diagnostic Tool in Patients with Benign and Malignant Ovarian Tumors", *Anticancer Research*, 19:2535-2536.
S.P. Treon et al., 1999, "Muc-1 Core Protein Is Expressed on Multiple Myeloma Cells and Is Induced by Dexamethasone", *Blood*, 93:1287-1298.
K. Ono et al., 1999, "The humanized anti-HM1.24 antibody effectively kills multiple myeolma cells by human effector cell-mediated cytotoxicity", *Mol. Immunology*, 36:387-395.
G. Teoh et al., 1998, "The 86kD Subunit of Ku Autoantigen Mediates Homotypic and Heterotypic Adhesion of Multiple Myeloma Cells", *J. Clin. Invest.*, 101:1379-1388.
W.C.A.M. Buijs et al., 1998, "Dosimetric analysis of chimeric monoclonal antibody cMOv18 IgG in ovarian carcinoma patients after intraperitoneal and intravenouse administration", *Eur. J. Nuclear Medicine*, 25:1552-1561.
M.A. Bookman, 1998, Biological Therapy of Ovarian Cancer: Current Directions:, *Seminars in Oncology*, 25:381-396.
M. Kawata et al., 1998, "Detection of Epithelial Ovarian-Cancer-Associated Antigens Involved in Immune Complexes by Monoclonal Antibodies", *Tumor Biology*, 19:1-11.
S.A. McQuarrie et al., 1997, "Pharmacokinetics and radiation dosimetry of $^{99}Tc^m$-labelled monoclonal antibody B43.13 in ovarian cancer patients", *Nuclear Medicine Communications*, 18:878-886.
E. Kievit et al., 1997, "Comparison of the Biodistribution and the Efficacy of Monoclonal Antibody 323/A3 Labeled with Either $^{131}$I or $^{186}$Re in Human Ovarian Cancer Xenografts", *Int. J. Radiation Oncology bio. Phys.*, 38:813-832.

(Continued)

*Primary Examiner*—Larry R. Helms
*Assistant Examiner*—Lei Yao
(74) *Attorney, Agent, or Firm*—Morgan & Finnegan, LLP

(57) ABSTRACT

The present invention is directed to cell surface antigens found on myeloma cells and on ovarian cancer cells, and monoclonal antibodies, and antibody binding fragments thereof, capable of being used for therapeutic, diagnostic, detection and cell purification purposes. An exemplified monoclonal antibody of the present invention recognizes and binds to an epitope common to surface antigen expressed on multiple myeloma cells and on ovarian cancer cells.

5 Claims, 8 Drawing Sheets

OTHER PUBLICATIONS

M. Hartman et al., 1999, "MUC1 Isoform Specific Monoclonal Antibody 6E6/2 Detects Preferential Expression of the Novel MUC1/Y Protein in Breast and Ovarian Cancer", *Int. J. Cancer*, 82-256-267.

M.L. Grossbard et al., 1998 "Anti-B4-blocked ricin: a phase II trial of 7 day continuous infusion in patients with multiple myeloma". *British Journal of Haematology*, 102:509-515.

H. Bertz et al., 1997, "Adoptive immunotherapy for relapsed multiple myeloma after allogeneic bone marrow transplantation (BMT): evidence for a graft-versus-myeloma effect", *Leukemia*, 11:281-283.

J.L. Hornick et al., 1997, "Chimeric CLL-1 antibody Fusion Proteins Containing Granulocyte-Macrophage Colony-Stimulating Factor or Interleukin-2 with Specificity for B-Cell Malignancies Exhibit Enhanced Effector functions while Retaining Tumor Targeting Properties", *Blood*, 89:4437-4447.

D.G. Maloney et al., 1999, "Antibody Therapy for treatment of Multiple Myeloma", *Seminars in Hematology (Suppl.)*, 36:30-33.

V. Nuessler et al., 1997, "Functional P-gp expression in multiple myeloma patients at primary diagnosis and relapse or progressive disease" *Leukemia (Suppl.)*, 11:S10-S14.

G.J. Ossenkoppele, 1997, "Treatment of Multiple Myeloma in Elderly Patients",. *Drugs & Aging*, 11:152-164.

T.H. Totterman et al., 1998, "Targeted Superantigens for Immunotherapy of Haematopoietic Tumors", *Vox Sanguinis*, 74:483-487.

M.G. Rosenblum et al., 1999, "Phase I Study of $^{90}$Y-labeled B72.3 Intraperitoneal Administration in Patients with Ovarian Cancer: Effect of Dose and EDTA Coadministration on Pharmacokinetics and Toxicity", *Clinical Cancer Research*, 5:953-961.

R.H.M. Verheijen et al., 1999, "CA 125: fundamental and clinical aspects", *Seminars in Cancer Biology*, 9:117-124.

G. Fleckenstein et al., 1998, "Monoclonal antibodies in solid tumours: approaches to therapy with emphasis on gynaecological cancer", *Medical Oncology*, 15:212-221.

E. Kievit et al., 1998 "[$^{186}$Re]-Labeled Mouse and Chimeric Monoclonal Antiboyd 323/A3: a Comparison of the Efficacy in Experimental Human Ovarian Cancer", *Nuclear Medicine & Biology*, 25:37-45.

S. Nicholson et al., 1998, "Radioimmunotherapy after chemotherapy compared to chemotherapy alone in the treatment of advanced ovarian cancer: A matched analysis", *Oncology Reports*, 5:223-226.

B.C. Schultes et al., 1998, Anti-idiotype induction therapy: anti-CA125 antibodies (Ab$_3$) mediated tumor killing in patients treated with Ovarex mAb B43.13 (Ab$_1$), *Cancer Immunol. Immunother*, 46:201-212.

M. Jojovic et al., 1998, "Epithelial glycoprotein-2 expression is subject to regulatory processes in epithelial-mesenchymal transitions during metastases: an investigation of human cancers transplanted into severe combined immunodeficient mice", *Histochemical Journal*, 30:723-729.

C. Kosmas et al., 1998, "Monoclonal Antibody Targeting of Ovarian Carcinoma", *Oncology*, 55:435-446.

M.F. Federici et al., 1999, "Selection of Carbohydrate Antigens in Human Epithelial Ovarian Cancers as Targets for Immunotherapy: Serous and Mucinous Tumors Exhibit Distinctive Patterns of Expression", *Int. J. Cancer*, 81:193-198.

W.G. McCluggage et al., 1998, "Immunocytochemical staining of ovarian cyst aspirates with monoclonal antibody against inhibin", *Cytopathology*, 9:336-342.

H.C.T. Van Zaanen et al., 1998, "Blocking Interleukin-6 Activity with Chimeric Anti-IL6 Monoclonal Antibodies in Multiple Myeloma: Effects on Soluble IL6 Receptor and Soluble gp 130", *Leukemia and Lymphoma*, 31:551-558.

V.L. Reichardt et al., 1997, "Rationale for adjuvant idiotypic vaccination after high-dose therapy for multiple myeloma", *Biol. Blood and Marrow Transplant*, 3:157-163.

N.L. Smith et al., 1999, "Immunohistochemically detecting target antigens in patient biopsies for tailoring monoclonal antibody based cancer therapy", *human Antibodies*, 9:61-65.

E. Harlow et al., 1988, "Labeling Antibodies", *Antibodies: A Laboratory Manual*, pp. 321-631.

N.S. Greenspan et al., 1999, "Defining epitopes: It's not as easy as it seems", *Nature Biotechnology*, 17:936-937.

P. Knight, 1989, "The Carbohydrate Frontier", *Biotechnology*, 7:35-40.

J.M. Cruse et al., 1995, *Illustrated Dictionary of Immunology*, p. 22.

W. Paul, 1993, *Fundamental Immunology*, Raven Press, NY Chpt 8, p. 242.

Partington K.M. et al.: "A Novel Method Of Cell Separation Based On Dual Parameter Immunomagnetic Cell Selection" *Journal of Immunological Methods*, vol. 223, No. 2; Mar. 4, 1999 pp. 195-205.

Tai Y -T et al.: "Isolation And Characterization Of Human Multiple Myeloma Cell Enriched Populations" *Journal of Immunological Methods*, vol 235, No. 1-2; Feb. 2000; pp.11-19.

\* cited by examiner

Differential screening of B cell hybridomas on myeloma vs. K562 cells by ELISA (pools of 4 hybridoma cultures)

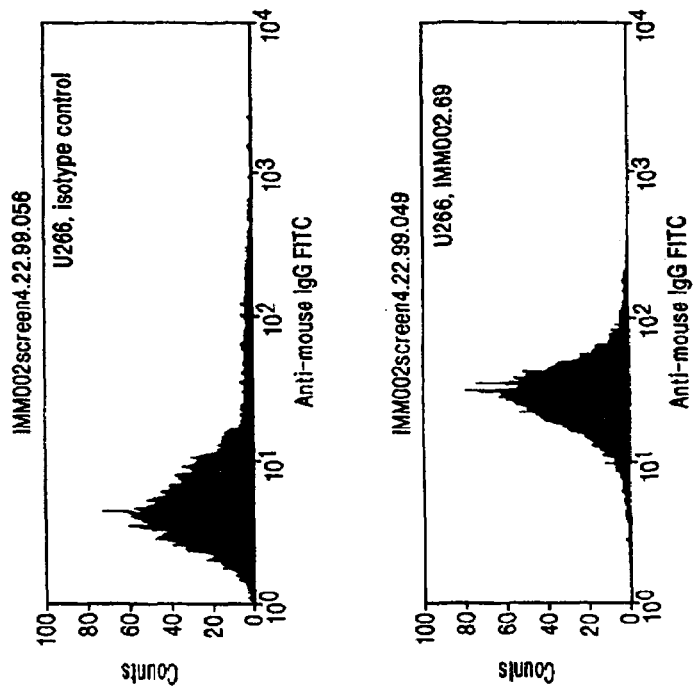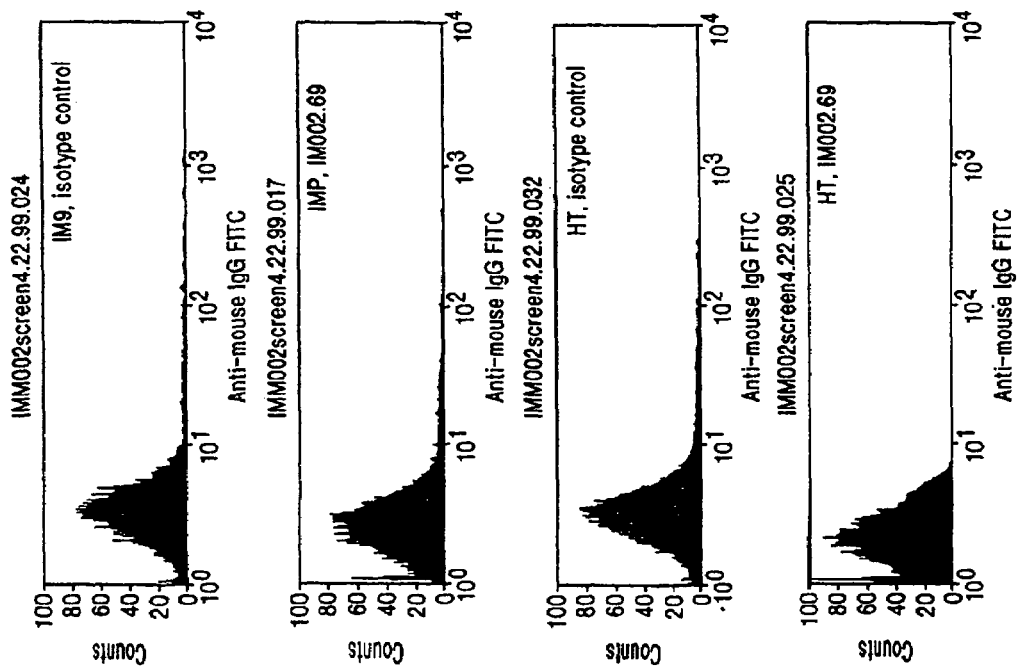
FIG. 4

MYELOMA CELL AND OVARIAN CANCER CELL SURFACE GLYCOPROTEINS, ANTIBODIES THERETO, AND USES THEREOF

This application is a continuation of U.S. application Ser. No. 09/995,522, filed Nov. 28, 2001 now U.S. Pat. No. 6,986,891 which is a divisional of U.S. application Ser. No. 09/374,367, filed Aug. 13, 1999, now U.S. Pat. No. 6,376,654 each of which is incorporated by reference herein in its entirety.

FIELD OF THE INVENTION

The application is related to new surface glycoproteins of human myeloma cells and human ovarian tumor cells, monoclonal antibodies thereto, and methods of diagnosis and treatment of myeloma and ovarian cancer based thereon.

BACKGROUND OF THE INVENTION

Multiple myeloma (MM) embodies a plasma cell disorder characterized by neoplastic proliferation of a single clone of plasma cells engaged in the production of a monoclonal immunoglobulin, usually monoclonal IgG or IgA. MM accounts for 1% of all malignant disease and slightly more than 10% of all hematologic malignancies. The annual incidence of multiple myeloma is 4 per 100,000. The annual incidence is linked to aging population. The median age of patients at the time of diagnosis is 61 years. MM is most common in men, and in individuals of African ancestry.

MM remains a disease for which a cure is a rarity. Most patients succumb to their disease within 36-48 months from the time of diagnosis. The limitations of effective therapy for MM are primarily associated with a low cell proliferation rate and multi-drug resistance. Therapy for multiple myeloma includes induction, maintenance, and supportive aspects. The induction portion of the treatment aims at reducing the tumor volume and achieving a plateau phase. Different drugs and treatment modalities, such as bone marrow transplantation, have been entertained, and used without a significant impact on the disease or the overall survival.

Supportive care in multiple myeloma has advanced significantly over the past few years. Growth factor support with erythropoietin replacement and GM-CSF for stimulating the white blood cell (WBC) population are safe and effective methods of decreasing or preventing the occurrence or the severity of neutropenia. Also, high dose chemotherapy followed by autologous bone marrow or peripheral blood progenitor cell (PBMC) transplantation has recently increased the complete remission rate and remission duration. However, overall survival has only been slightly prolonged, and no evidence for a cure has been obtained. All patients ultimately relapse, even under maintenance therapy with interferon-α (IFN-α) alone or in combination with steroids. Adoptive immunotherapy rather than active vaccination may prove to be a more effective therapy for MM patients. There are relatively few known surface antigens on plasma cells that are suitable for antibody-directed treatment. Possible molecules include HM1.24, CD38, ICAM-1 (CD54), CD40, CD45, CD20, and syndecan 1. To date, there are no exclusive markers reported for MM. CD20, CD38, CD56 and CD130 are all markers that are expressed on normal B-cells, T-cells, or natural killer (NK) cells.

Ovarian cancer is the fifth leading cause of cancer deaths among U.S. women and has the highest mortality of any of the gynecologic cancers. It accounted for an estimated 26,600 new cases and 14,500 deaths in 1995. The overall 5-year survival rate is at least 75%, if the cancer is confined to the ovaries, and decreases to 17% in women diagnosed with distant metastases. Symptoms usually do not become apparent until the tumor compresses or invades adjacent structures, or ascites develops, or metastases become clinically evident. As a result, two thirds of women with ovarian cancer have advanced (Stage III or IV) disease at the time of diagnosis. Carcinoma of the ovary is most common in women over age 60. Other important risk factors include low parity and a family history of ovarian cancer. Less than 0.1% of women are affected by hereditary ovarian cancer syndrome, but these women may face a 40% lifetime risk of developing ovarian cancer.

Potential screening tests for ovarian cancer include the bimanual pelvic examination, the Papanicolaou (Pap) smear, tumor markers, and ultrasound imaging. The pelvic examination, which can detect a variety of gynecologic disorders, is of unknown sensitivity in detecting ovarian cancer. Although pelvic examinations can occasionally detect ovarian cancer, small, early-stage ovarian tumors are often not detected by palpation due to the deep anatomic location of the ovary. Thus, ovarian cancers detected by pelvic examination are generally advanced and associated with poor survival. The pelvic examination may also produce false positives when benign adnexal masses (e.g., functional cysts) are found. The Pap smear may occasionally reveal malignant ovarian cells, but it is not considered to be a valid screening test for ovarian carcinoma. Ultrasound imaging has also been evaluated as a screening test for ovarian cancer, since it is able to estimate ovarian size, detect masses as small as 1 cm, and distinguish solid lesions from cysts.

Serum tumor markers are often elevated in women with ovarian cancer. Examples of these markers include carcinoembryonic antigen, ovarian cystadenocarcinoma antigen, lipid-associated sialic acid, NB/70K, TAG 72.3, CA15-3, and CA-125, respectively. Evidence is limited on whether tumor markers become elevated early enough in the natural history of occult ovarian cancer to provide adequate sensitivity for screening. Tumor markers may have limited specificity. It has been reported that CA-125 is elevated in 1% of healthy women, 6-40% of women with benign masses (e.g., uterine fibroids, endometriosis, pancreatic pseudocyst, pulmonary hamartoma) and 29% of women with nongynecologic cancers (e.g., pancreas, stomach, colon, breast). Prospective studies involving asymptomatic women are needed, however, to provide definitive data on the performance characteristics of serum tests when used as screening tests.

SUMMARY OF THE INVENTION

In its broadest aspect, the present invention is directed to a monoclonal antibody, or binding fragment thereof, which specifically binds to antigens sharing a common epitope present on the surface of human myeloma cells and ovarian cancer cells. The antigen on multiple myeloma cells is a single glycosylated polypeptide with a molecular weight of about 78 kDa to about 120 kDa, as determined by SDS-PAGE under reducing conditions. The antigen on ovarian cancer cells is a single glycosylated polypeptide with a molecular weight of about 76 kDa to about 213 kDa, as determined by SDS-PAGE under reducing conditions. The antigens are absent from human peripheral blood mononuclear cells, absent from human B cells, and absent from human chronic myelogenous leukemia cells. A non-limiting example of the monoclonal antibody is that produced by the hybridoma cell line deposited at the American Type Culture Collection (ATCC), 10801 University Boulevard, Manassas, Va. 20110-

2209, having accession No. PTA-450. Furthermore, the antigens are not present on cells from a breast cancer tumor, not present on a prostate cancer cell line, not present on a neuroblastoma cell line, and not present on a cervical cancer cell line. The antigens are also not found on an Epstein-Barr virus-transformed B cell tumor.

The present invention is further directed to antibodies that are capable of binding to the same antigenic determinant as does the monoclonal antibody produced by the hybridoma cell line deposited at the American Type Culture Collection having accession No. PTA-450; binding fragments of the hybridoma cell line deposited at the American Type Culture Collection having accession No. PTA-450; and to binding fragments of a monoclonal antibody capable of binding to the same antigenic determinant as does the monoclonal antibody produced by the hybridoma cell line deposited at the American Type Culture Collection having accession No. PTA-450.

Such monoclonal antibodies, or antibody fragments, may be human, or they may be derived from other mammalian species, such as rodent, hybrids thereof, chimeric antibodies, and the like. Binding fragments of the monoclonal antibodies of the present invention include, but are not limited to, F(ab')$_2$, Fab', Fv, Fd', or Fd fragments.

In another aspect, the present invention is directed to a cell line produced by a hybridoma technique, which produces a monoclonal antibody which specifically binds to surface antigens of human myeloma cells and of ovarian cancer cells. The antigen on multiple myeloma cells is a single glycosylated polypeptide with a molecular weight of about 78 kDa to about 120 kDa as determined by SDS PAGE under reducing conditions. The antigen on ovarian cancer cells is a single glycosylated polypeptide with a molecular weight of about 76 kDa to about 213 kDa, as determined by SDS-PAGE under reducing conditions. The antigens are absent from human peripheral blood mononuclear cells, absent from human B cells, and absent from human chronic myelogenous leukemia cells. A non-limiting example of a monoclonal antibody according to the present invention is that produced by the hybridoma cell line deposited at the American Type Culture Collection having accession No. PTA-450. Furthermore, the antigens are not present on cells from a breast cancer tumor, not present on a prostate cancer cell line, not present on a neuroblastoma cell line, and not present on a cervical cancer cell line. The antigens are also not found on an Epstein-Barr virus-transformed B cell tumor.

A further aspect of the present invention is the hybridoma cell line deposited at the American Type Culture Collection having accession No. PTA-450.

Hybridoma cell line producing monoclonal antibody IMM002.69.47.4 has been deposited with the American Type Culture Collection (ATCC, P.O. Box 1549, Manassas, Va. 20108) on Aug. 3, 1999 under the provisions of the Budapest Treaty on the International Recognition of the Deposit of Microorganisms for the Purposes of Patent Procedures, and assigned accession numbers PTA-450, and incorporated herein by reference.

In another broad aspect of the present invention, an isolated surface antigen of human multiple myeloma cells is described, the antigen being a single glycosylated polypeptide with a molecular weight of about 78 kDa to about 120 kDa, as determined by SDS-PAGE under reducing conditions; the antigen being absent from human peripheral blood mononuclear cells, absent from human B cells, and absent from human acute myelogenic leukemia cells. The antigen is not present on cells from a breast cancer tumor, not present on a prostate cancer cell line, not present on a neuroblastoma cell line, and not present on a cervical cancer cell line. It is also not found on an Epstein-Barr virus-transformed B cell tumor. The isolated multiple myeloma surface antigen binds to a monoclonal antibody produced by the hybridoma cell line deposited at the American Type Culture Collection having accession No. PTA-450.

In another broad aspect of the present invention, an isolated surface antigen of human ovarian cancer cells is described, the antigen being a single glycosylated polypeptide with a molecular weight of about 76 kDa to about 213 kDa, as determined by SDS-PAGE under reducing conditions; the antigen being absent from human peripheral blood mononuclear cells, absent from human B cells, and absent from human acute myelogenic leukemia cells. The antigen is not present on cells from a breast cancer tumor, not present on a prostate cancer cell line, not present on a neuroblastoma cell line, and not present on a cervical cancer cell line. It is also not found on an Epstein-Barr virus-transformed B cell tumor. The isolated ovarian cancer surface antigen binds to a monoclonal antibody produced by the hybridoma cell line deposited at the American Type Culture Collection having accession No. PTA-450.

The present invention is also directed to methods of inhibiting the growth of, or killing, myeloma cells in a patient by administering the monoclonal antibody, or a binding fragment as described above, under conditions sufficient for the binding of the monoclonal antibody, or the binding fragment, to the myeloma cells to cause inhibiting or killing of the cancer cells by the immune cells of the patient. In another aspect, a method for inhibiting or killing myeloma cells in a patient is provided by administering the monoclonal antibody, or binding fragment as described above, which is conjugated with a cytotoxic moiety, under conditions sufficient for the binding of the monoclonal antibody, or binding fragment, to the cancer cells to inhibit the growth of, or to kill, the cells. The cytotoxic moiety may be, by way of non-limiting example, a chemotherapeutic agent, a photo-activated toxin or a radioactive agent.

In still another aspect of the invention, the above-mentioned conjugate of the monoclonal antibody, or binding fragment, described herein and a cytotoxic moiety may be used in vitro to inhibit growth of, or kill, myeloma cells in a cellular sample, such as a bone marrow sample.

The invention is also directed to anti-idiotypic antibodies which mirror the binding site of the monoclonal antibody of the invention, and are specific to the myeloma and ovarian cancer conformational epitope recognized by the antibody of the invention. The invention is further directed to the use of the aforementioned anti-idiotypic antibodies for the treatment of MM or ovarian cancer by active immunization.

In a further aspect of the invention, a method is provided for removing myeloma cells from an isolated cellular sample, such as, but not limited to, bone marrow cells, by exposing the cellular sample to a solid matrix on which the monoclonal antibody, or binding fragment, described above is bound under conditions wherein the myeloma cells adhere to the monoclonal antibody, or binding fragment, and isolating a cellular fraction of said cellular sample which does not bind to the matrix. This method may be used, for example, in the removal of myeloma cells from a bone marrow sample for autologous bone marrow transplant.

The invention is also directed to the monoclonal antibody, or binding fragment, as described above bound to a solid support.

In yet another aspect of the invention, a method is provided for localizing myeloma cells or tumor cells, or ovarian cancer cells or tumor cells, in a patient by administering the monoclonal antibody, or binding fragment, as described above, allowing the monoclonal antibody, or binding fragment thereof, to bind to the cancer cells within said patient, and determining the location of the monoclonal antibody, or binding fragment thereof, within the patient. In another related aspect, the monoclonal antibody, or binding fragment, is detectably labeled, for example, with a radionuclide.

The present invention is further directed to methods of inhibiting the growth of, or killing, ovarian cancer cells in a patient by administering the monoclonal antibody, or binding fragment, as described above under conditions sufficient for the binding of the monoclonal antibody, or binding fragment, to the ovarian cancer cells to cause growth inhibition or killing of the ovarian cancer cells by immune cells of the patient. In another aspect, a method for inhibiting or killing ovarian cancer cells in a patient is provided by administering the monoclonal antibody, or binding fragment, as described above which is conjugated with a cytotoxic moiety, under conditions sufficient for the binding of the monoclonal antibody, or binding fragment, to ovarian cancer cells to cause growth inhibition or killing of the ovarian cancer cells. The cytotoxic moiety may be, by way of non-limiting example, a chemotherapeutic agent, a photo-activated toxin, or a radioactive agent.

In yet another aspect of the invention, a method is provided for localizing ovarian cancer cells in a patient by administering the monoclonal antibody, or binding fragment, described above, allowing the monoclonal antibody, or binding fragment thereof, to bind to ovarian cancer cells within said patient, and determining the location of said monoclonal antibody, or binding fragment thereof, within said patient. In another related aspect, the monoclonal antibody, or binding fragment, is detectably labeled, for example, with a radionuclide.

It is a further aspect of the invention to permit the detection of the cell surface glycoproteins described herein in a sample of bodily fluid, to aid in the diagnosis of multiple myeloma, ovarian cancer, or other cancer cells expressing a glycoprotein with the epitope recognized by the antibodies herein, by the detection of the glycoprotein antigen shed from cancer cells into the bodily fluid, such as blood. Furthermore, the stage of the disease may be monitored and the effectiveness of anti-cancer therapies can be monitored by determining the level or changes over time of the level of shed surface glycoprotein in a bodily fluid such as blood.

In still yet another aspect, the invention is directed to pharmaceutical compositions comprising a monoclonal antibody, or binding fragment, as described above and a pharmaceutically-acceptable carrier, diluent, or excipient.

In another aspect, the present invention is directed to a monoclonal antibody, or binding fragment, as described above labeled with a detectable moiety, such as, by way of non-limiting examples, a fluorophore, a chromophore, a radionuclide, or an enzyme.

These and other aspects of the present invention will be better appreciated by reference to the following drawings and Detailed Description.

BRIEF DESCRIPTION OF THE DRAWINGS

FIG. 4 presents the results of cell surface staining using a panel of monoclonal antibodies and analyzed by flow cytometry.

DETAILED DESCRIPTION OF THE INVENTION

Figure 1:
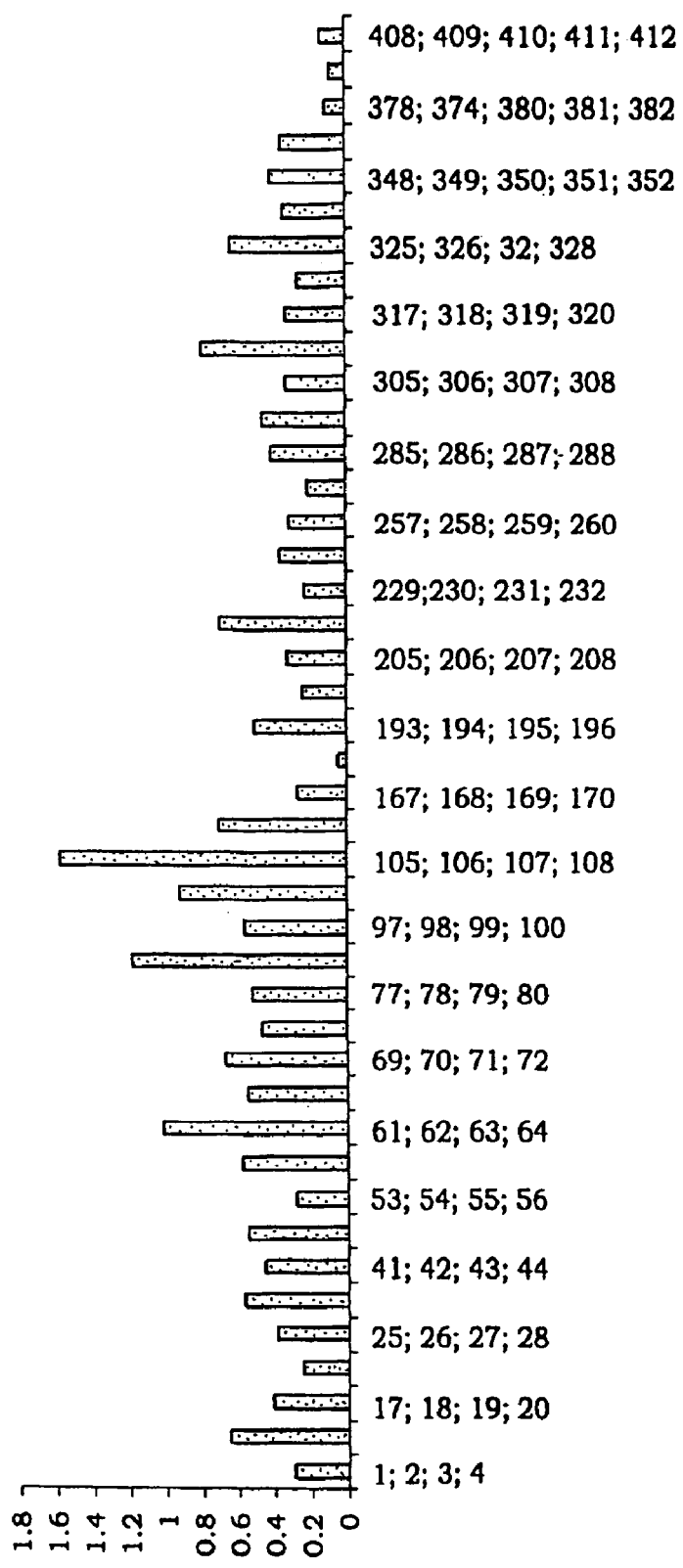
FIG. 1 depicts a first screen of B cell hybridomas generated from mice immunized with a pool of three human plasmacytoma cells compared with their binding to human myelogenic leukemia cell line (K562), which serves as a control.

Identification of unique cancer antigens enables the design of selective immunotherapy for neoplastic diseases. The capacity to utilize a determinant exclusively expressed by cancer cells, and which is devoid in normal tissues, ensures the targeting and elimination of the neoplastic cells while insulating the function of normal cells. Although the last decades have witnessed great activity and significant success in the search for novel cancer antigens for various neoplastic diseases, cancer-specific antigens have not yet been defined for many malignancies. The majority of cancer antigens are self-antigens that are derived from and expressed by normal counterpart cells. Frequently, the cancer antigen is identical to the normal antigen even though it is expressed at higher levels, or endowed with a negligible mutation insufficient for its distinction from the self-antigen. One of the escape mechanisms of malignant cells from the immune system is their similarity to their normal counterpart cells, thus resulting in low visibility of the malignant cells by the immune system.

New surface glycoprotein antigens that are present on human myeloma cells and human ovarian cancer tumor cells, but absent from normal cells and from leukemic cells, are provided by the present invention. Such antigens present a target for therapeutic intervention in myeloma and ovarian cancer, as well as for diagnostic and cell purification purposes. These antigens share at least one common epitope.

A technique known as contrasting immunization was employed for obtaining monoclonal antibodies to the antigen and for the identification of the novel cancer antigens described herein. As described in the examples below, two divergent immunogens provided at different locations were used. The dual immunization polarizes the migration of the distinct populations of immune cells to discrete draining lymph nodes. In an example herein, a mixture of human myeloma cells was used as the immunogen to obtain murine monoclonal antibodies to a myeloma cell surface antigen. Control cells in this example, i.e., a related, myelogenic leukemic cell line, were used to polarize the immune response to effectively delete undesired cells from the lymph nodes near the site of immunization with the desired antigen. The immune cells extracted from the draining lymph nodes close to the immunization site with the desired neoplasms were immortalized by fusion with murine myeloma cells. The antipodal draining lymph nodes were populated with immune cells specific to the undesired (control) immunogens.

By use of the foregoing protocol, a series of monoclonal antibodies were prepared which were found to bind specifically to antigens on the surfaces of human myeloma cells and on ovarian cancer cells. These antigens share at least one epitope. The antigens are further characterized in that the antigen on multiple myeloma cells is a single glycosylated polypeptide with a molecular weight of about 78 kDa to about 120 kDa, as determined by SDS-PAGE under reducing conditions; and it is absent from human peripheral blood mononuclear cells, absent from human B cells, and absent from human B cell myelogenic leukemia cells.

The antigen on ovarian cancer cells is a single glycosylated polypeptide with a molecular weight of about 76 kDa to about 213 kDa, as determined by SDS-PAGE under reducing conditions; and it is absent from human peripheral blood mononuclear cells, absent from human B cells, and absent from human B cell myelogenic leukemia cells. An antigen recognized by the antibody of the invention is also present on liver cancer cells; thus, the liver cancer cell surface antigen has at least one epitope in common with the myeloma and ovarian cancer surface glycoprotein. An example of a hybridoma cell line that produces a monoclonal antibody which recognizes these antigens has been deposited at the American Type Culture Collection, and accorded accession No. PTA-450.

The aforementioned antigens were found not to be present on cells from a breast cancer tumor, and were not present on a prostate cancer cell line, or on a neuroblastoma cell line, or on a cervical cancer cell line. They were also not found on an Epstein-Barr virus-transformed B cell tumor.

The present invention is directed to monoclonal antibodies, and binding fragments thereof, which recognize the aforementioned myeloma cell and ovarian cancer cell surface glycoproteins. Thus, the present invention embraces the deposited monoclonal antibody described above and monoclonal antibodies and their binding fragments having binding specificity for the aforementioned antigens. Such antibody fragments capable of binding the aforementioned antigens, include, but are not limited to, F(ab')$_2$ fragments, Fab' fragments, Fv fragments, Fd' fragments, or Fd fragments. Antibodies may be human, mammalian, such as mouse, and hybrid or chimeric antibodies. The antibody fragments and means for preparing then from antibodies are known to one of skill in the art.

The monoclonal antibodies and antibody binding fragments may be characterized as those which are 1) produced from the hybridoma cell line deposited at the American Type Culture Collection having accession No. PTA-450; 2) capable of binding to the same antigenic determinant as does the monoclonal antibody produced by the hybridoma cell line deposited at the American Type Culture Collection having accession No. PTA-450; 3) binding fragments of the hybridoma cell line deposited at the American Type Culture Collection having accession No. PTA-450; or 4) binding fragments of a monoclonal antibody capable of binding to the same antigenic determinant as does the monoclonal antibody produced by the hybridoma cell line deposited at the American Type Culture Collection having accession No. PTA-450.

Accordingly, the aforementioned monoclonal antibodies and binding fragments recognize a common epitope of cell surface glycoproteins present on human myeloma cells and on human ovarian cancer cells, but absent from human peripheral blood mononuclear cells, absent from human B cells, and absent from human B cell myelogenic leukemia cells. Further, the cell surface glycoprotein on myeloma cells is a single polypeptide with a molecular weight of about 78 kDa to about 120 kDa, as determined by SDS-PAGE under reducing conditions. The cell surface glycoprotein on ovarian cancer ells is a single polypeptide with a molecular weight of about 76 kDa to about 213 kDa, as determined by SDS-PAGE under reducing conditions. As the myeloma, ovarian cancer, and liver cancer cell surface glycoproteins share a common epitope recognized by the antibodies of the invention, such antibodies may be used therapeutically and diagnostically for these conditions. As mentioned above, the antigen is also present on the surface of liver cancer cells, but is not present on cells from a breast cancer tumor, not present on a prostate cancer cell line, not present on a neuroblastoma cells line, and not present on a cervical cancer cell line. It is also not found on an Epstein-Barr virus-transformed B cell tumor.

The present invention is also directed to hybridoma cell lines which produce a monoclonal antibody which specifically binds to the surface antigens of human myeloma cells and ovarian cancer cells as described and characterized herein. These antigens have a shared region or an epitope contained in the cell surface glycoproteins of these neoplasms. The methods for the preparation of such hydridomas are known to the skilled artisan. The contrasting immunization procedure described herein is but one example of various means for obtaining the desired antibodies. For preparation of monoclonal antibodies directed toward the surface glycoprotein antigens described herein, any technique that provides for the production of antibody molecules by continuous cell lines in culture may be used. For example, such techniques include, but are not limited to, the hybridoma technique originally developed by Kohler and Milstein (*Nature,* 256:495-497, 1975), as well as the trioma technique, the human B-cell hybridoma technique (Kozbor et al., *Immunology Today,* 4:72, 1983; Cote et al., *Proc. Natl. Acad. Sci. U.S.A.,* 80:2026-2030, 1983), and the EBV-hybridoma technique to produce human monoclonal antibodies (Cole et al., in *Monoclonal Antibodies and Cancer Therapy,* Alan R. Liss, Inc., pp. 770-96, 1985).

In another embodiment of the present invention, monoclonal antibodies can be produced in germ-free animals utilizing the technology described in international application number WO 98/02545. Also, according to the invention, techniques developed for the production of "chimeric antibodies" are suitable for use. Preferred are human or humanized chimeric antibodies for use in therapy of human diseases or disorders as described infra, since the human or humanized antibodies themselves are much less likely than xenogenic antibodies to induce an immune response, particularly an allergic response.

According to the present invention, techniques described for the production of single chain antibodies (U.S. Pat. Nos. 5,476,786 and 5,132,405 to Huston; and U.S. Pat. No. 4,946,778) can be adapted to produce myeloma surface antigen-specific single chain antibodies. An additional embodiment of the invention utilizes the techniques described for the construction of Fab expression libraries (Huse et al., *Science,* 246:1275-1281, 1989) to allow the rapid and easy identification of monoclonal Fab fragments with the desired specificity, or fragment derivatives, or analogs.

Antibody fragments which contain the idiotype of the antibody molecule can also be generated by known techniques. For example, such fragments include, but are not limited to, the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

As mentioned above, the present invention is also directed to the isolated surface antigens of human myeloma cells and human ovarian cancer cells, wherein the human myeloma cell-expressed antigen is characterized as being a single glycosylated polypeptide with a molecular weight of about 78 kDa to about 120 kDa, as determined by SDS-PAGE under reducing conditions and the human ovarian cancer cell-expressed antigen is characterized as having a molecular weight of about 76 kDa to about 213 kDa. These antigens are absent from human peripheral blood mononuclear cells, absent from human B cells, and absent from human B cell myelogenic leukemia cells. The antigens are also absent from breast cancer cells, as determined using fresh tumor tissue; absent from prostate cancer cells, determined using a prostate cancer cell line; absent from neuroblastoma cells, as determined using a neuroblastoma cell line, and absent from cervical cancer cells as determined by using a cervical cancer cell line. The glycoproteins have been found to be present on the surfaces of cells from a freshly-isolated liver cancer tumor. Thus, the above-described methods are also applicable to the therapy and diagnosis of liver cancer. The isolated surface antigens are further characterized in that they bind to the monoclonal antibody produced by the hybridoma cell line deposited at the American Type Culture Collection having accession No. PTA-450.

The monoclonal antibody MA69 reacts consistently with a single chain glycoprotein with a molecular weight of 78-120 kDa on multiple myeloma (MM) cells. On ovarian carcinoma cells, however, MA69 recognizes one or more glycoproteins ranging in size from 76 to 213 kDa. These results imply that MA69 reacts with two distinct molecules expressed on MM and ovarian cancer cells through the recognition of a shared region or an epitope contained in the cell surface glycoproteins of these neoplasms. This epitope is uniquely expressed on cells of ovarian and MM malignancies and was not found on the cell surfaces of a panel of human tumors, such as lung cancer, cervical cancer, neuroblastoma, breast cancer, prostate cancer, leukemia and lymphomas. Thus, the present invention is also generally directed to cell surface glycoproteins which comprise an epitope recognized by the antibodies of the invention. As noted above, cell surface glycoproteins comprising this epitope are absent from the various normal and cancer cells tested and listed above.

The present invention is also directed to therapeutic methods for the treatment of myeloma and related dysproliferative diseases in humans, including multiple myeloma, as well as ovarian cancer, using the antibodies of the present invention. The therapeutic and diagnostic uses described herein embrace primary tumors as well as metastases. For example, a method for inhibiting or killing myeloma cells or ovarian cancer cells in a patient may be carried out by administering to the patient, in a single dose or in successive doses, the monoclonal antibody, or antibody binding fragment as described above, under conditions sufficient for the binding of the monoclonal antibody, or binding fragment, to tumor cells in the patient. Binding of antibodies to the tumor cells induces the growth inhibition and/or killing of the tumor cells by immune cells in the patient.

The aforementioned therapy may be accompanied by other treatments directed at the tumor cells, such as chemotherapy, radiation, etc., as well as by adjunctive therapies to enhance the immune system's attack on the opsonized tumor cells following the procedure described above. For example, a growth factor such as erythropoietin and/or GM-CSF can be co-administered to the patient for stimulating the white blood cells and supporting the immunocompetence status of the patient.

Further, chimeric or other recombinant antibodies of the invention may be used therapeutically. For example, a fusion protein comprising at least the antigen-binding region of the antibody of the invention joined to at least a functionally active portion of a second protein having anti-tumor effects, e.g., a lymphokine or oncostatin, may be used to treat a human tumor in vivo. In addition, a chimeric antibody, wherein the antigen-binding site is joined to human Fc region, e.g., IgGI, may be used to promote antibody-dependent mediated cytotoxicity or complement-mediated cytotoxicity. In addition, recombinant techniques known in the art can be used to construct bispecific antibodies wherein one of the binding specificities is that of the antibody of the invention (See, e.g., U.S. Pat. No. 4,474,893).

It will be appreciated by the skilled practitioner that other dysproliferative diseases in which the glycoprotein antigens of the invention are present on the cell surface are treatable by the methods described herein.

The above-described methods utilize the antibodies or binding fragments without modification, relying on the binding of the antibodies or fragments to the surface antigen(s) of the myeloma or ovarian cancer cells in situ to stimulate an immune attack thereon. In another aspect of the therapeutic methods, the aforementioned method may be carried out using the monoclonal antibodies or binding fragments to which a cytotoxic agent is bound. Binding of the cytotoxic antibodies, or antibody binding fragments, to the tumor cells inhibits the growth of or kills the cells. By way of non-limiting example, suitable cytotoxic agents may be a chemotherapeutic agent, a photo-activated toxin or radioactive agent. For example, cytotoxic agents such as ricin A chain, abrin A chain, modeccin A chain, gelonin, melphalan, bleomycin, adriamycin, daunomycin, or pokeweed antiviral proteins (PAP, PAPII, PAP-S).

Those skilled in the art will realize that there are numerous radioisotopes and chemocytotoxic agents that can be coupled to tumor specific antibodies by well known techniques, and delivered to specifically destroy tumor tissue. See, e.g., U.S. Pat. No. 4,542,225 to Blattler et al. Examples of photo-activated toxins include dihydropyridine- and omega-conotoxin (Schmidt et al., *J Biol. Chem.*, 1991, 266(27):18025-33). Examples of imaging and cytotoxic reagents that can be used include $^{125}$I, $^{111}$In, $^{123}$I, $^{99m}$Tc, $^{32}$P, $^{3}$H, and $^{14}$C; fluorescent labels such as fluorescein and rhodamine, and chemiluminescers such as luciferin. The antibody can be labeled with such reagents using techniques known in the art. For example, see Wenzel and Meares, *Radioimmunoimaging and Radioimmunotherapy*, Elsevier, N.Y. (1983) for techniques relating to the radiolabeling of antibodies (see also, Colcer et al., "Use of Monoclonal Antibodies As Radiopharmaceuticals For The Localization Of Human Carcinoma Xenografts In Nude Mice", *Methods Enzymol.*, 121:802-16,1986: "Order, Analysis, Results and Future Prospective of the Therapeutic Use of Radiolabeled Antibody in Cancer Therapy", in *Monoclonal Antibodies for Cancer Detection and Therapy*, Baldwin et al. (eds), pp. 303-16 (Academic Press 1985).

Other covalent and non-covalent modifications of the antibodies or antibody fragments of the present invention are embraced herein, including agents which are co-administered or administered after the antibody or fragments, to induce growth inhibition or killing of the cells to which the antibody or fragment has previously bound.

Anti-idiotypic monoclonal antibodies to the antibodies of the invention may also be used therapeutically in active tumor immunization and tumor therapy (see, e.g., Hellstrom et al., "Anti Idiotypes" in *Covalently Modified Antigens and Antibodies in Diagnosis and Therapy*, supra at pp. 35-41).

In the area of multiple myeloma, the antibodies or antibody fragments of the present invention have further utility in the preparation of cellular samples from which myeloma cells have been removed. This use is particularly important in autologous bone marrow transplants, wherein a sample of bone marrow is harvested from a cancer patient prior to the patient's undergoing high-dose chemotherapy. The goal of the high dose chemotherapy is to destroy the cancer cells, which also results in the depletion of bone marrow cells. Following such treatment, the harvested bone marrow cells are reintroduced into the patient.

In myeloma and related diseases, the harvested bone marrow is contaminated with myeloma cells; thus, reintroduction of untreated bone marrow will simply reintroduce the disease. Previous methods to prevent reintroduction of cancer cells have included treatment of the bone marrow sample with chemotherapeutic agents and other anti-neoplastic agents in vitro. Other methods include purging the sample of cancer cells.

In a further practice of the present invention, the monoclonal antibodies and fragments described herein may be used to remove myeloma cells from a patient's bone marrow sample before reintroduction into the patient. In one nonlimiting example, the monoclonal antibodies, or binding fragments, are attached to a matrix, such as beads. This may be accomplished by any of several well-known methods for preparing an affinity matrix comprising antibodies or their binding fragments. The bone marrow sample is then exposed to the matrix, such as by passage of the cells over a column containing the matrix, under conditions to promote the binding of the myeloma cells in the sample through antigen/antibody interactions with the antibodies or binding fragments attached to the matrix. The myeloma cells in the sample adhere to the matrix; while the column effluent, i.e., the non-adherent cellular population, is depleted of myeloma cells. The effectiveness of the procedure may be monitored by examining the cells for residual myeloma cells, such as by using a detectably-labeled antibody as described below. The procedure may be repeated or modified to increase effectiveness.

This purging procedure (see, e.g., Ramsay et al., *J Clin. Immunol.*, 8(2):81-88, 1988) may be performed together with other methods for removing or killing cancer cells, including, but not limited to, exposing the purified bone marrow cells to chemotherapeutic agents. Such chemotherapeutic agents include the use of the antibodies or antibody binding fragments of the present invention conjugated to a cytotoxic agent, as those described above for in vivo therapeutic treatment. Accordingly, conjugates of the antibodies or antibody fragments of the present invention with cytotoxic agents may be used for the ex vivo killing of tumor cells in a cellular sample. The methods may additionally include exposing the cells to cytokines (e.g., GM-CSF, IL-6), cytokine receptors (e.g., IL-6-receptor), mitogens (e.g., poke weed mitogen (PWM)), or adhesion molecules (e.g., CD40 ligand) in order to stimulate the myeloma cells to rapidly differentiate and thereby upregulate expression of cancer-specific antigens on their cell surface. These treatment modalities are intended to render the myeloma cells vulnerable to the in vitro- mediated cytotoxicity achieved by incubation with the monoclonal antibody, or fragments thereof, according to the present invention.

In another aspect of the therapeutic methods of the present invention, the antibodies, or binding fragments thereof, conjugated with cytotoxic agents, such as chemotherapeutic agents, a photo-activatable toxin, or a radionuclide, may be used in vitro or ex vivo to inhibit or kill myeloma cells from a bone marrow sample, in the absence of the purging technique described above. The treatment of a sample with the cytotoxic antibodies, or antibody fragments, may be combined with other methods to kill cancer cells to increase the effectiveness of a bone marrow transplant, particularly an autologous bone marrow transplant, by removing cells from the tissue to be transplanted. These methods may include additionally exposing the cells to cytokines, etc. Thus, a method is described herein for removing myeloma cells from a isolated cellular sample comprising the steps of exposing the cellular sample to a solid matrix on which a monoclonal antibody, or antibody binding fragment as described herein, is bound under conditions in which the myeloma cells adhere to the monoclonal antibody, or binding fragment thereof, and isolating a cellular fraction of the cellular sample which does not bind to the matrix. By way of non-limiting example, bone marrow cells are used, particularly for a transplant, and preferably, an autologous bone marrow transplant.

In a further aspect of the present invention, compositions are provided which comprise the monoclonal antibody, or antibody binding fragment as described herein, bound to a solid support. A solid support for use in the present invention will be inert to the reaction conditions for binding. A solid phase support for use in the present invention must have reactive groups or activated groups in order to attach the monoclonal antibody or its binding partner thereto. In another embodiment, the solid phase support may be a useful chromatographic support, such as the carbohydrate polymers SEPHAROSE®, SEPHADEX®, or agarose. As used herein, a solid phase support is not limited to a specific type of support. Rather, a large number of supports are available and are known to one of ordinary skill in the art. Solid phase supports include, for example, silica gels, resins, derivatized plastic films, glass beads, cotton, plastic beads, alumina gels, magnetic beads, membranes (including, but not limited to, nitrocellulose, cellulose, nylon, and glass wool), plastic and glass dishes or wells, etc.

The present invention is also directed to diagnostic and imaging methods for multiple myeloma and ovarian cancer using the monoclonal antibodies and binding fragments thereof as described hereinabove. Other cancers bearing the surface antigens of the invention are also amenable to these diagnostic procedures. The method involves administration or infusion of monoclonal antibodies or binding fragments as described herein, with or without conjugation to a detectable moiety, such as a radionuclide. After administration or infusion, the antibody, or antibody fragment, binds to the tumor cells, after which the location of the antibodies, or fragments, is detected. For detectably-labeled antibodies or their binding fragments, such as those labeled with a radionuclide, imaging instrumentation may be used to identify the location of the agent within the body. For use of unlabeled antibodies or fragments, a second, detectable reagent may be administered which locates the antibodies or antibody fragments, and thus may be suitably detected. These methods have been used for other antibodies, and the skilled artisan will be amply aware of these various methods for imaging the location of antibodies or fragments within the body.

In the case of ovarian cancer, as well as other cancers expressing the antigens described herein, the present invention is further directed to the diagnosis of cancer by the identification and measurement of shed cell surface glycoprotein in bodily fluids, such as blood, serum, or plasma. As ovarian cancer is a particularly difficult cancer to diagnose in its early stages, thus thwarting the opportunity for early treatment, methods for early diagnosis are particularly needed. Measurement of shed surface glycoprotein in a whole blood sample, for example, by use of an antibody, or fragment thereof, of the invention provides such early diagnosis and the opportunity for treatment. Such treatment may comprise the foregoing antibody-based therapy, in combination with other agents, or the use of such agents in the absence of the antibodies of the invention.

Furthermore, the level of shed ovarian cancer antigen measured in blood or other bodily fluids provides a means for monitoring the course of ovarian cancer therapy, including surgery, chemotherapy, radiation therapy, and the therapeutic methods of the present invention. By correlating the level of shed antigen with the severity of disease, the level of shed antigen can be used to indicate successful removal of the primary tumor and/or metastases, and the effectiveness of other therapies over time. A decrease in the level over time indicates a reduced tumor burden in the patient. In contrast, no change, or an increase in level, indicates ineffectiveness of therapy or the continued growth of the tumor.

The present invention is also directed to pharmaceutical compositions comprising a monoclonal antibody, or binding fragment thereof, which specifically binds to an antigen on the surface of a human myeloma cell, the antigen being further characterized as described hereinabove, together with a pharmaceutically-acceptable carrier or diluent. The invention is further directed to pharmaceutical compositions comprising a monoclonal antibody, or binding fragment thereof, including the monoclonal antibody produced from the hybridoma cell line deposited at the American Type Culture Collection having accession No. PTA-450; antibodies that are capable of binding to the same antigenic determinant as does the monoclonal antibody produced by the hybridoma cell line deposited at the American Type Culture Collection having accession No. PTA-450; binding fragments of the hybridoma cell line deposited at the American Type Culture Collection having accession No. PTA-450; and binding fragments of a monoclonal antibody capable of binding to the same antigenic determinant as does the monoclonal antibody produced by the hybridoma cell line deposited at the American Type Culture Collection having accession No. PTA-450; and a pharmaceutically-acceptable carrier, excipient, or diluent. Antibody fragments include but are not limited to $F(ab')_2$ fragments, Fab' fragments, Fv fragments, Fd' fragments, or Fd fragments.

A pharmaceutical composition includes a pharmaceutically acceptable carrier, excipient, or diluent. Preferably, the antibodies or binding fragments thereof are delivered parenterally, such as by intravenous administration. Alternative modes of administration include, but are not limited to, subcutaneous, intraperitoneal, oral, intranasal, intrathecal, rectal, of intramuscular administration, and the like. Suitable buffers, carriers, and other components known to those in the art are used in formulating a composition comprising the antibody, or fragments thereof, for suitable shelf-life and compatibility with administration. These substances may include ancillary agents such as buffering agents and protein stabilizing agents (e.g., polysaccharides).

The antibodies of the present invention are also useful for diagnostic applications, both in vitro and in vivo, for the detection of human multiple myeloma and ovarian cancer cells that possess the antigen for which the antibodies are specific. In vitro diagnostic methods include immunohistological detection of tumor cells (e.g., on human tissue cells for excised tumor specimens), or serological detection of tumor-associated antigens (e.g., in blood samples or other biological fluids). Immunohistochemical techniques involve staining a biological specimen such as tissue specimen with the antibody of the invention and then detecting the presence of antibody complexed to its antigen as an antigen-antibody complex. The formation of such antibody-antigen complexes with the specimen indicates the presence of multiple myeloma cells in the tissue. Detection of the antibody on the specimen can be accomplished using techniques known in the art such as immunoenzymatic techniques, e.g., immunoperoxidase staining technique, or the avidin-biotin technique, or immunofluorescence techniques (see, e.g., Ciocca et al., "Immunohistochemical Techniques Using Monoclonal Antibodies", Methods Enzymol, 121:562-79, 1986 and Kimball, (ed), Introduction to Immunology ($2^{nd}$ Ed), pp. 113-117 (Macmillan Pub. Co., 1986).

Serologic diagnostic techniques involve the detection and quantification of tumor-associated antigens that have been secreted or "shed" into the serum or other biological fluids of patients thought to be suffering from multiple myeloma. Such antigens can be detected in the body fluids using techniques known in the art such as radioimmunoassay (RIA) or enzyme-linked immunoabsorbant assays (ELISA) wherein antibody reactive with the "shed" antigen is used to detect the presence of the antigen in a fluid sample (see, e.g., Uotila et al., "Two-Site Sandwich ELISA With Monoclonal Antibodies to Human AFP", J Immunol. Methods, 42:11, 1981 and Allum et al., supra, at pp 48-51). Detection of the shed ovarian cancer antigen can be performed as described above.

Also as mentioned above, the antibodies of the present invention are useful for the measurement of shed ovarian cancer cell antigen in bodily fluids such as whole blood, serum, or plasma, for the diagnosis of ovarian cancer and the monitoring of the effectiveness of therapies.

In yet a further aspect of the present invention, monoclonal antibodies, or binding fragments thereof, having specificity for myeloma surface glycoprotein and ovarian cancer glycoprotein, as described, are labeled with a detectable moiety so that they can be used to diagnose or identify cells having the aforementioned antigens. Non-limiting examples of such labels include fluorophores, such as fluorescein isothiocyanate; chromophores, radionuclides, or enzymes. Such labeled antibodies or binding fragments may be used for the histological localization of the antigens, for ELISA, for cell sorting, and for other immunological techniques to detect and/or quantify the antigens, and cells bearing the antigens, for example. As noted above, a particular use of such labeled antibodies, or fragments thereof, is in determining the effectiveness of myeloma cell depletion from bone marrow tissue prior to transplant, particularly autologous bone marrow transplant.

EXAMPLES

The present invention may be better understood by reference to the following non-limiting Examples, which are provided as exemplary of the invention. The following examples are presented in order to more fully illustrate the preferred embodiments of the invention and should in no way be construed to limit the broad scope of the invention.

Example 1

Preparation and Screening of Hybridomas

1. Sources of cells. Human myeloma cell lines (U266, OPM, RPMI1860, KR12 and NCI H929), and chronic myelogenic leukemic cell line (K562) were purchased from the American Type Culture Collection (ATCC). Fresh human ovarian cancer, breast cancer, and liver cancer specimens were used. Cell lines of prostate cancer, LnCap (ATCC); neuroblastoma cell line, NCI H2106 (ATCC); and a cervical cancer, Caski (ATCC) were also evaluated, as well as an EBV-transformed B cell tumor, Namalwa (ATCC).

2. Immunization. Mice were immunized with a pool of plasmacytoma cells, U266, RPMI1860 and OPM ($5\times10^6$ total in 50 µl containing Ribi adjuvant, 50%), in the left footpad, and with K562 cells ($5\times10^6$ total in 50 µl containing Ribi adjuvant, 50%) in the right footpad. The immunization was repeated after 14 days. The left popliteal lymph node was removed and the extracted cells were fused 3 days after the second immunization.

3. Generation of B cell hybridomas. Monoclonal antibodies specific to multiple myeloma cells were produced by conventional methods. Popliteal (left) lymph node cells from immunized mice were fused with a mouse myeloma cell line (Sp2/0) in the presence of polyethylene glycol (PEG) to form hybridomas which were capable of producing monoclonal antibodies that specifically bound to human plasmacytoma cells.

4. Cellular ELISA—Flow cytometry analysis. Various human tumor cell lines grown in in vitro culture were washed and stained with a panel of monoclonal antibodies selected on the basis of cellular ELISA screen. After 30 minutes of incubation on ice, the cells were washed and incubated with Rabbit anti-mouse IgG monoclonal antibody conjugated with fluorescein isothiocyanate (FITC). The mean intensity of the fluorescence was determined by flow cytometry using the FACScaliber (Becton and Dickinson). Histograms plotting the intensity of the staining correlated with cell count demonstrated the specificity of monoclonal antibody 69 (MA69) to human plasmacytoma cells.

5. Western blot analysis. SDS-PAGE gels were prepared from stock solutions of 30% acylamide/0.8% bisacrylamide. TRIS-HCl/SDS, pH 8.8, sterile distilled $H_2O$, 10% (w/v) ammonium persulfate and TEMED were added, following standard procedures. A stacking gel was included if the samples were greater than 10 µl in volume. Surface membrane proteins from cells were prepared for electrophoresis by the following protocol: Cells from in vitro cultures were collected and washed. The cells were lysed following 3 repeated cycles of freeze-thaw (−80° C. and 37° C.). The lysates were stored at −20° C. until use. Membranes were prepared from cell lysates following a 30 minute centrifugation at 2500 rpm. The supernatant consisting of cytosolic protein and membranes was further separated by centrifugation at 40,000 rpm using an ultracentrifuge. The pellet containing the membrane fraction was collected and stored at −20° C.

Proteins were separated at 150 V for about 1.5 hours at 4° C. After separation, the proteins were transferred onto nitrocellulose in a Transfer box at 22 V run overnight at 4° C. The nitrocellulose was blocked using BLOTTO A® for 45 minutes at room temperature, reacted first with primary antibody for 45 minutes at room temperature, followed by washing and reaction with the appropriate secondary antibody conjugated to horseradish peroxidase. After washing, Amersham ECL reagents were used for detection.

The results of a first screen of B cell hybridomas generated from mice immunized as described above are shown in FIG. 1. The method of the screen was cellular ELISA which tested the binding of the supernatants removed from B cell hybridoma cultures to a pool of human plasmacytoma cells in one well, compared with their binding to human myelogenic leukemia cell line (K562), which served as a control. Net binding was calculated as the absorbance recorded for binding to the pool of human plasmacytoma cells after subtraction of binding to the K562 control cell line. In the initial screen, a pool of 4 hybridomas was tested in each well. Hybridoma pools that recorded high levels of differential binding were selected and then each hybridoma was tested individually.

Figure 2:
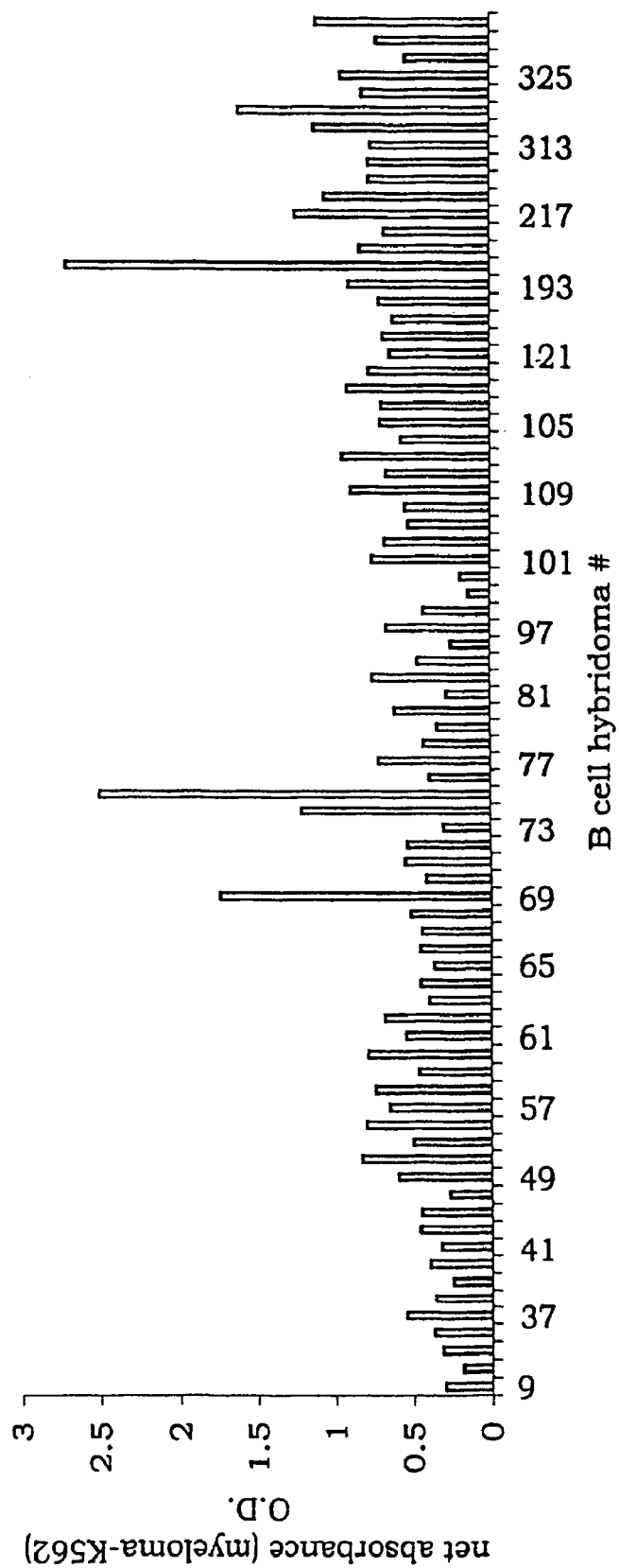
FIG. 2 presents the result of selected hybridomas for the second screen.

No binding to cells from a fresh breast cancer tumor, a prostate cancer cell line, a neuroblastoma cell line, or a cervical cancer cell line was detected. In addition, no binding to an EBV-transformed B cell tumor was detected. FIG. 2 presents the results of selected hybridomas for the second screen. Hybridoma numbers 69, 75, and 194, i.e, MoAb 69, 75 and 194, showed specificity, compared with K562 cells.

Figure 3:
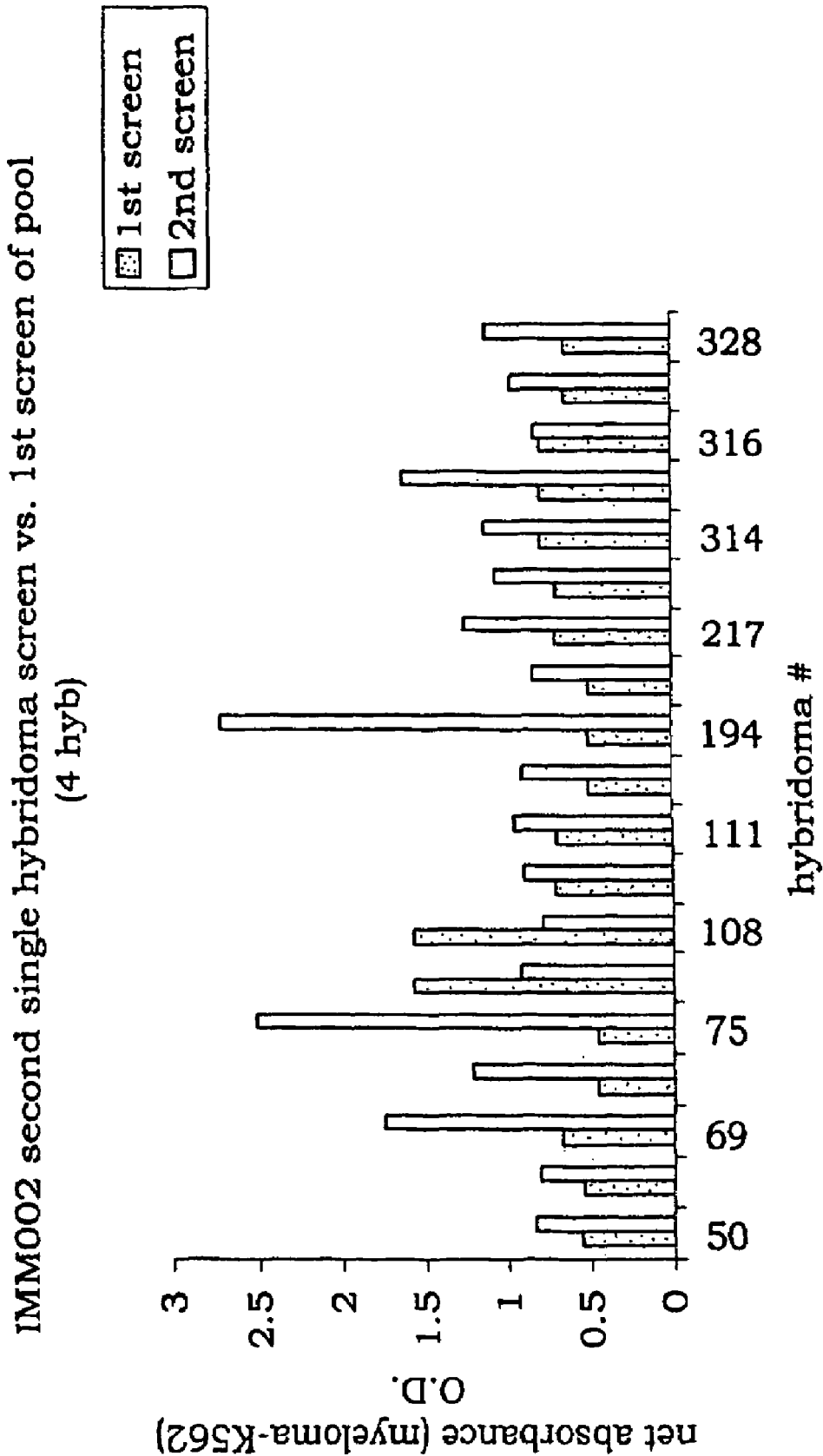
FIG. 3 depicts the net binding values obtained for the first screen compared with the second screen.

In a further analysis of the above data, the net binding values (O.D.) obtained for the first screen compared with the second screen are shown in FIG. 3.

Example 2

Specificity Assessment of Monoclonal Antibodies

Cell surface staining using a panel of monoclonal antibodies Jul. 16, 1999 analyzed by flow cytometry is depicted in FIG. 4. A strong staining of plasmacytoma cells by MA69 is demonstrated in panel F, while negative staining was demonstrated for the control cell lines, including human B cell tumor lines IM9 and HT (IM9 with isotype control, panel A; IM9 with MA69, panel B; HT with isotype control, panel C; HT with MA69, panel D) and myeloma cell line U266 with an isotype control monoclonal antibody (panel E). Furthermore, peripheral blood cells (PBMC) from normal individuals showed insignificant binding to the antibodies.

Hybridoma cell line IMM002.69.47.4 which produces monoclonal antibody MA69 was deposited on Aug. 3, 1999, with the American Type Culture Collection, 10801 University Boulevard, Manassas Va. 20110-2209, and has been assigned PTA-450.

Example 3

Binding of Monoclonal Antibody to Cell Surface Glycoprotein

B cell hybridoma culture designated MA69 was shown to detect a distinct band on myeloma membranes from five human multiple myeloma cell lines (RPMI1860, U266, KR-12, OPM-1 and NCl H929) using Western blots. Four of the five myeloma cell lines showed binding to a cell surface glycoprotein with an approximate molecular weight of between about 78 and about 120 kDa. The PBMC serving as a negative control did not show binding to the antibody. In addition, no staining of two human B cell tumors (HT and IM9) was observed (FIG. 5).

Figure 5:
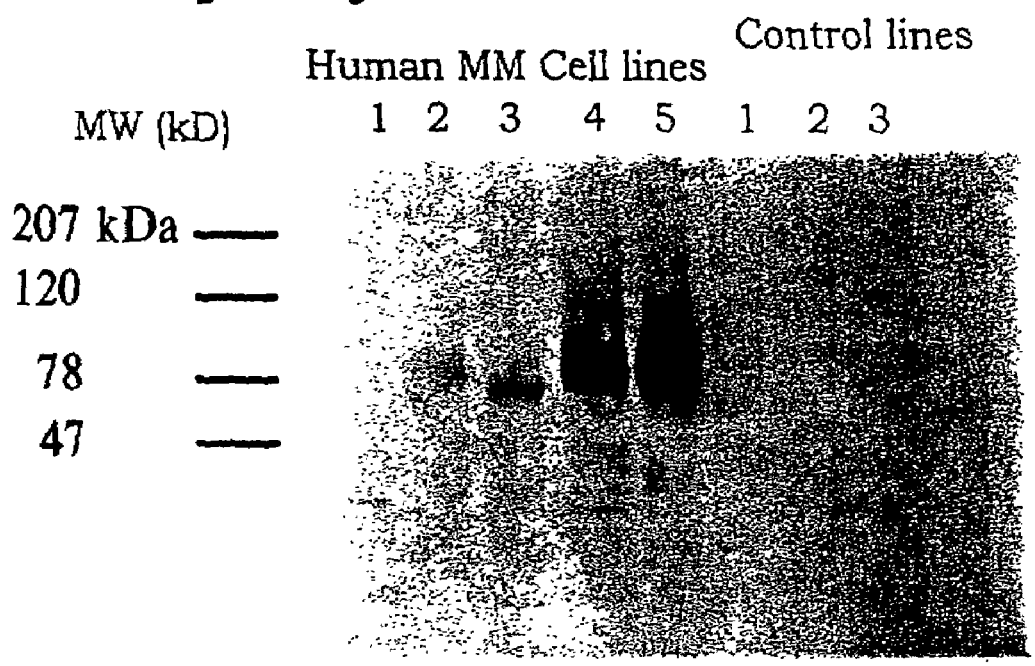
FIG. 5 represents further evaluation of the selected monoclonal antibodies using Western blot method, using membrane proteins extracted from five human myeloma cell lines tested individually, and controls, fractionated on SDS-PAGE.
Figure 6:
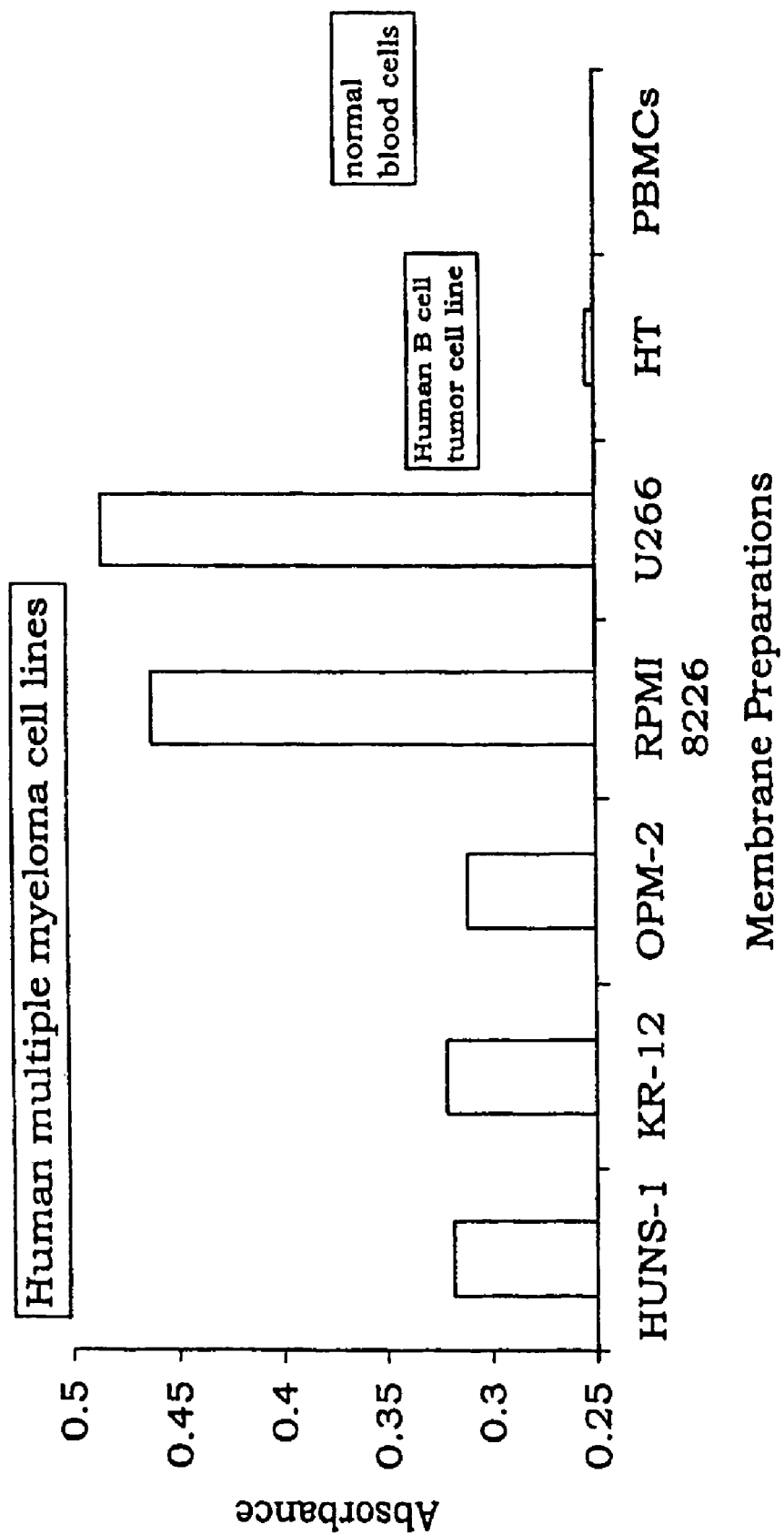
FIG. 6 presents results similar to those described for FIG. 5, using a cellular ELISA method.

FIG. 6 graphically presents the results of a repeat of the experiment described in FIG. 5 using a cellular ELISA method. In this experiment, the MA69 detected a distinct band on 5 out of 5 myeloma cell lines with varying intensities. The control membrane preparations consisting of normal PBMC and a human B cell tumor (HT) were not stained by the antibody.

Example 4

Detection of Shed Surface Glycoprotein from Cultured Myeloma Cells

Figure 7:
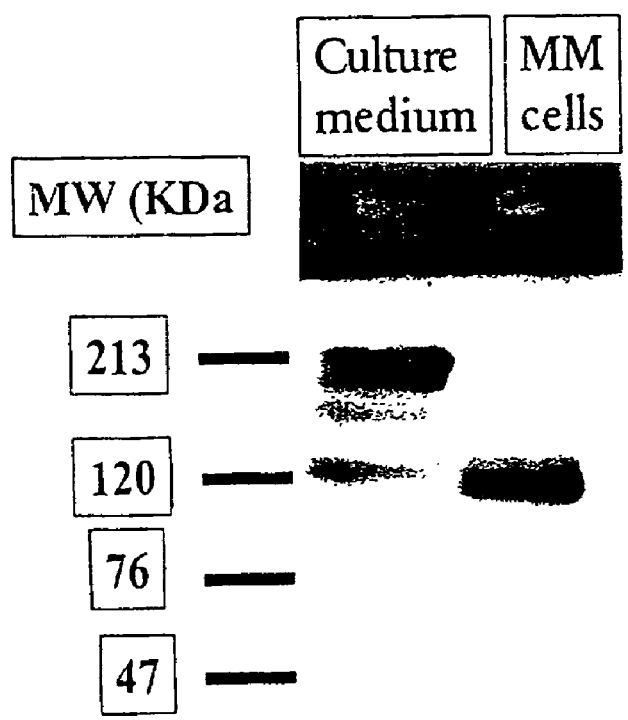
FIG. 7 shows an SDS-PAGE gel of concentrated culture fluid from multiple myeloma cells grown in serum-free medium for 5 days, blotted and probed with an antibody of the present invention.

Human myeloma cells were grown in AIM V serum-free medium for 5 days. The medium was collected and concentrated ten-fold using a Centricon device (Amersham). As a control, a cell lysate was prepared from MM cultured in vitro and fractionated by SDS-PAGE. Concentrated growth medium was fractionated coincidently as a control. Blotting and probing with MA69 demonstrated the presence of the surface glycoprotein in the medium (FIG. 7, left lane).

Example 5

Surface Glycoprotein Present on the Surface of Human Ovarian Cancer Cells

Figure 8:
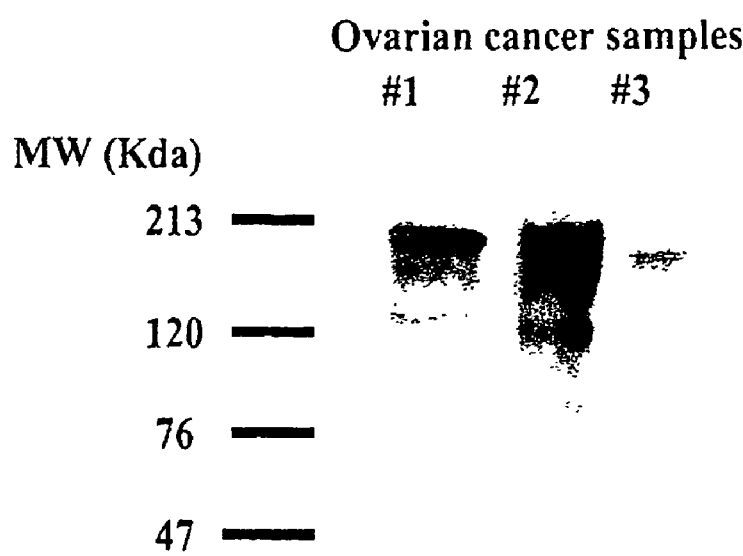
FIG. 8 depicts SDS-PAGE results of cell lysates from three ovarian cancer tumor cells from 3 patient. The tumor cells were digested with trypsin and homogenized. The gel was blotted and probed with an antibody of the present invention.

Three ovarian cancer tumors from three patients were digested with trypsin and homogenized. The cell lysates were fractionated by SDS-PAGE. The gel was blotted and probed with MA69 monoclonal antibody. As shown in FIG. 8, the surface glycoprotein of the invention is expressed on these cells. The antigen on ovarian cancer cells is a single glycosylated polypeptide with a molecular weight of about 76 kDa to about 213 kDa, as determined by SDS-PAGE under reducing conditions. The ovarian cancer cell antigen shares at least one epitope with the aforementioned multiple myeloma surface antigen.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Various publications, patents, references, and the like, are cited herein, the disclosures of which are incorporated herein by reference in their entireties.

What is claimed is:

1. A method for monitoring the effectiveness of therapy for a myeloma or ovarian cancer, comprising:
    a) measuring changes in the level of the antigen recognizable by a monoclonal antibody or antigen binding fragment thereof in a bodily fluid sample from a patient undergoing therapy, wherein said monoclonal antibody is produced by the hybridoma cell line deposited at the American Type Culture Collection having accession No. PTA-450; and
    b) correlating the change in the level with the effectiveness of said therapy, wherein a decrease in the level indicates a reduced tumor burden.

2. The method of claim 1, wherein the antigen binding fragment is F(ab')2, Fab', Fv, Fd', or Fd.

3. The method of claim 1, further comprising labeling the monoclonal antibody or antigen binding fragment thereof with a detectable moiety.

4. The method of claim 3, wherein the detectable moiety is a fluorophore, a chromophore, a radionuclide, or an enzyme.

5. The method of claim 1, wherein the bodily fluid is blood, serum, or plasma.

* * * * *